United States Patent [19]

Dao

[11] Patent Number: 5,471,705
[45] Date of Patent: Dec. 5, 1995

[54] CAUTERIZER BLADE WIPING DEVICE

[75] Inventor: Leland H. Dao, Haleiwa, Hi.

[73] Assignee: Devon Industries, Inc., Chatsworth, Calif.

[21] Appl. No.: 236,264

[22] Filed: May 2, 1994

Related U.S. Application Data

[63] Continuation-in-part of Ser. No. 11,173, Jan. 29, 1993, abandoned, which is a continuation-in-part of Ser. No. 908,412, Jul. 6, 1992, abandoned.

[51] Int. Cl.$^6$ .................................................. A47L 25/00
[52] U.S. Cl. ........................ 15/236.05; 15/218; 15/218.1; 15/236.01; 15/236.09
[58] Field of Search .................................. 15/218, 218.1, 15/220.4, 221, 236.01, 236.05–236.09, 245; 131/240.1, 241; D27/104, 133; D32/46, 40, 35; D24/217

[56] References Cited

U.S. PATENT DOCUMENTS

| | | | |
|---|---|---|---|
| D. 74,297 | 1/1928 | Compton | D27/104 |
| D. 174,737 | 5/1955 | Coughlin | D27/133 |
| D. 198,613 | 7/1964 | McDorman | D27/133 |
| D. 203,957 | 3/1966 | Benes | D27/133 |
| D. 287,296 | 12/1986 | Yasuda | D27/133 |
| D. 309,206 | 7/1990 | Kelley | D32/46 |
| 708,262 | 9/1902 | Schweitzer | 15/218 |
| 718,822 | 1/1903 | Dakin | 15/218 |
| 1,212,185 | 1/1917 | Cobb | 131/241 |
| 1,219,933 | 3/1917 | Omoto | 15/218.1 |
| 1,256,282 | 2/1918 | Akerlund | 15/218 |
| 1,705,004 | 3/1929 | Dick | 15/281 |
| 1,802,569 | 4/1931 | Neahr | 131/240.1 |
| 2,213,046 | 8/1940 | Mather . | |
| 2,632,906 | 3/1953 | Friedman | 15/236.05 |
| 2,787,395 | 4/1957 | Florio | 15/236.07 |
| 2,803,030 | 8/1957 | Florio | 15/245 |
| 2,823,406 | 2/1958 | Beaulieu | 15/236.07 |
| 3,094,730 | 7/1963 | Schwarz | 15/218.1 |
| 3,372,419 | 3/1968 | Howey | 15/218.1 |
| 3,396,421 | 8/1968 | Rade | 15/236.09 |
| 3,667,079 | 6/1972 | Hagglund | 15/220.4 |
| 3,982,357 | 9/1976 | Eldridge et al. | 15/218.1 |
| 4,011,693 | 3/1977 | Eldridge, Jr. et al. | 15/218.1 |
| 4,017,935 | 4/1977 | Hernandez | 15/220.4 |
| 4,103,388 | 8/1978 | Devitis | 15/220.4 |
| 4,164,054 | 8/1979 | Hanson et al. | 15/220.4 |
| 4,325,158 | 4/1982 | Divish et al. | 15/218.1 |
| 4,374,445 | 2/1983 | Wilson | 15/220.4 |
| 4,543,751 | 10/1985 | Alikhan | D24/217 |
| 4,547,923 | 10/1985 | DeVries et al. | 15/218.1 |
| 4,704,760 | 11/1987 | Grieshaber | 15/218.1 |
| 4,752,983 | 6/1988 | Grieshaber | 15/218.1 |
| 4,896,393 | 1/1990 | Avila, Jr. | 15/220.4 |
| 4,925,516 | 5/1990 | Phillips et al. | 15/218.1 |
| 4,947,476 | 8/1990 | Seaburg | 15/220.4 |
| 4,958,403 | 9/1990 | Martin | 15/236.09 |
| 4,996,800 | 3/1991 | Mangus | 15/218.1 |

FOREIGN PATENT DOCUMENTS

| | | | |
|---|---|---|---|
| 20311 | 7/1915 | Denmark | 15/218.1 |
| 1439144 | 4/1966 | France . | |
| 3637599 | 5/1988 | Germany | 15/236.08 |
| 330614 | 7/1958 | Switzerland | 15/220.4 |
| 17093 | of 1891 | United Kingdom | 15/218.1 |
| 16169 | of 1893 | United Kingdom | 131/240.1 |
| 2243762 | 11/1991 | United Kingdom | 15/220.4 |

Primary Examiner—Mark Spisich
Attorney, Agent, or Firm—Lyon & Lyon

[57] ABSTRACT

A body, which may have a tubular or dome-like shape with an open top and bottom, has a wall with one or more elongated slots extending along the wall from the top toward the bottom. A cauterizer blade may be drawn through a slot in any suitable orientation to wipe debris from the blade. A mounting, such as a pressure-sensitive adhesive sheet, may be used to attach the body to a surgical drape. A slot may have two parallel inner edges for wiping or scraping the cauterizer blade. The distance between the inner edges defines the slot width, which should be approximately equal to the width of the cauterizer blade to be cleaned. The sides of the slot may be beveled to form chisel-like inner edges that enhance the wiping action. At the top of the body the slot may also have a "V"-shaped notch to guide the cauterizer blade into the slot. The adhesive sheet may be attached to the open bottom of the dome-shaped body. Both sides of the adhesive sheet may be coated with adhesive to both adhere the body to the surgical drape and to trap in the adhesive any debris that falls into the body.

8 Claims, 1 Drawing Sheet

CAUTERIZER BLADE WIPING DEVICE

CROSS-REFERENCES TO RELATED APPLICATIONS

This is a continuation-in-part of application Ser. No. 08/011,173 filed Jan. 29, 1993, now abandoned, which is a continuation-in-part of application Ser. No. 07/908,412, filed Jun. 6, 1992, now abandoned.

BACKGROUND OF THE INVENTION

The present invention relates to devices used for wiping burned tissue debris, known as eschar, from a surgical cautery knife blade.

Surgical instruments such as cautery knives, cautery pencils and various other cautery device tips often become soiled with particles of tissue, blood and other debris during a surgical intervention. The accumulation of these materials on the instrument can severely hinder its use. Surgeons must repeatedly wipe the instrument tip with gauze or scrape the tip with a scalpel during surgery. This procedure, however, requires that the surgeon or an assistant interrupt the operation to clean the instrument, using both hands and taking great care to avoid accidental cuts and injury. This cleaning procedure is not only very disruptive to the surgery, but also does not allow for a safe and convenient place to safely dispose of the excess burned tissue debris or eschar.

U.S. Pat. No. 4,547,923, issued to De Vries et al., discloses a surgical knife cleaner consisting essentially of a closely coiled strand supported on a base member bonded by adhesive to a surgical drape. The surgical knife blade is cleaned by insertion through adjacent coils of the device. This type of surgical knife cleaner, however, does not provide sufficient frictional pressure against the sides of the knife blade to completely rid it of eschar debris. Moreover, this type of surgical knife cleaner requires that penetration of the blade through the coil be in a single direction imposed by the orientation of the device.

Other cauterizer blade cleaning devices use sponge-like abrasive material as a wiping surface. After repeated use, eschar debris tends to build up on the abrasive material, thereby reducing its effectiveness and requiring other methods for further cleaning.

There is a need for a more versatile type of surgical instrument cleaner that is accessible from multiple directions, that provides a more thorough wiping action against soiled side of instrument blades, and that provides a means for containing scraped tissue debris for convenient disposal. These problems and deficiencies are clearly felt in the art and are solved by the present invention in the manner described below.

SUMMARY OF THE INVENTION

The present invention comprises a body having a wall with one or more elongated slots having sidewalls extending between the inner and outer surfaces of the wall and having a slot length extending in a longitudinal direction from an edge of the wall. The wall may have any suitable shape and contours. A cauterizer blade may be drawn through a slot in any suitable orientation to wipe debris from the blade. The orientation of the blade in the slot may be described by an angle of incidence and a pivotal angle with respect to a longitudinal axis of the slot.

The body also has one or more portions defining a planar area oriented at an angle with respect to the longitudinal axis of the slot. The present invention also comprises a mounting that may be used to attach the body to a suitable surface, such as a surgical drape, with the planar area parallel to the surface. In an exemplary embodiment, the mounting comprises a pressure-sensitive adhesive sheet. When the body is mounted on a surgical drape, for example, the slot and surrounding wall are oriented at a convenient angle with respect to the patient. The angled wall functions in a shield-like manner to enhance retention of debris behind the inner surface of the wall over a wide range of blade angles of incidence.

The shape of the slot is critical to one aspect of the present invention. A sidewall of the slot is bounded by a longitudinal inner edge along the inner surface of the wall and a longitudinal outer edge along the outer surface of the wall. Each of the two surfaces of the cauterizer blade contacts one inner edge when the blade is drawn through the slot, thereby wiping or scraping the blade. The distance between the inner edges defines the slot width, which should be approximately equal to the width of the cauterizer blade. The distance between the outer edges is greater than the slot width. For example, the sidewalls may be planar and thus have a beveled appearance. This arrangement allows the cauterizer blade to be positioned in the slot at any pivotal angle in a wide range, with each blade surface in contact with an inner edge. In addition, this arrangement provides chisel-like inner edges that enhance the wiping action. At the edge of the wall the slot may also have a notch having a suitable shape, such as a "V", to guide the cauterizer blade into the slot.

The wall may have any suitable shape that, when the body is mounted on a surface, is maintained in the above-described orientation. In an exemplary embodiment, the body is generally dome-shaped with an open top and bottom. The wall thus has a curved, annular or tubular shape with circular rims defining the open top and bottom of the body. One or more slots extend longitudinally from the upper rim toward the lower rim. When a cauterizer blade is drawn through a slot, debris falls into the open circular area in the center of the body. In such an embodiment, the lower circular rim may define the above-described planar area. A pressure-sensitive adhesive sheet covering the lower circular rim may thus be used to attach the body to a surgical drape or other surface. Furthermore, the adhesive sheet may be double-sided to retain debris that falls into the open central area by trapping it in the exposed adhesive.

The wall may have other suitable shapes, such as a sector of the above-described annular or tubular shape. It need not, however, be curved along two radii of curvature such as to define a dome or sector thereof; it may be curved along only a single radius of curvature to define a ring or sector thereof; or it may be entirely or partially planar. Furthermore, the wall may have any suitable contours or thicknesses. For example, it may have a generally convex outer surface, such as that of a dome-shaped body, with a concave portion or trough between the convex portions for catching any debris that may accumulate around a slot and fall or trickle down the outer surface of the wall. In an annular wall having a plurality of slots distributed around its circumference, such a trough may extend around the circumference of the wall.

The foregoing, together with other features and advantages of the present invention, will become more apparent when referring to the following specification, claims, and accompanying drawings.

BRIEF DESCRIPTION OF THE DRAWINGS

For a more complete understanding of the present invention, reference is now made to the following detailed description of the embodiments illustrated in the accompanying drawings, wherein.

DESCRIPTION OF A PREFERRED EMBODIMENT

Figure 1:
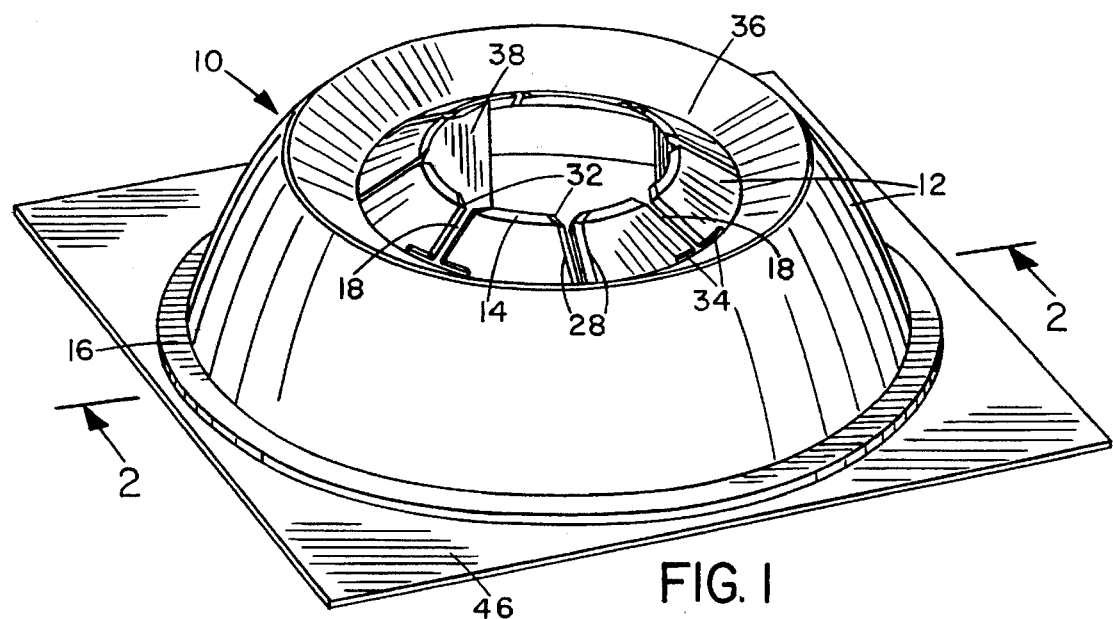
FIG. 1 is a perspective view of the cauterizer blade cleaner.
Figure 2:
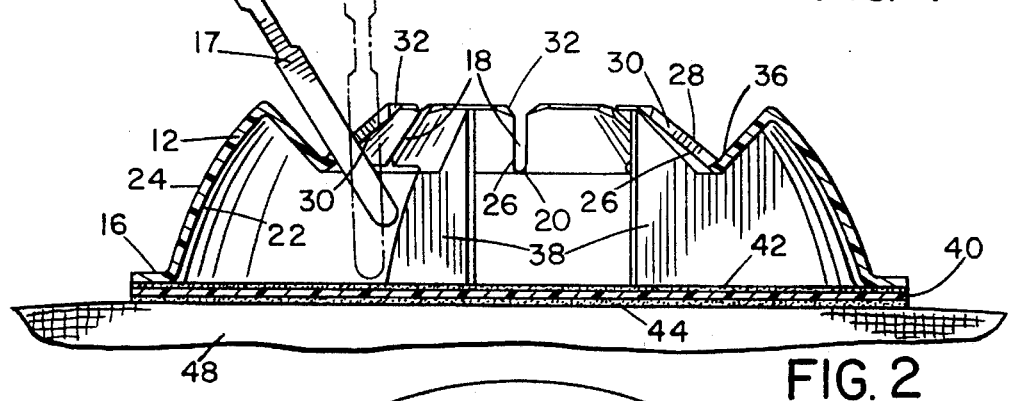
FIG. 2 is a sectional view taken along line 2—2 of FIG. 1, showing the cleaning method.
Figure 3:
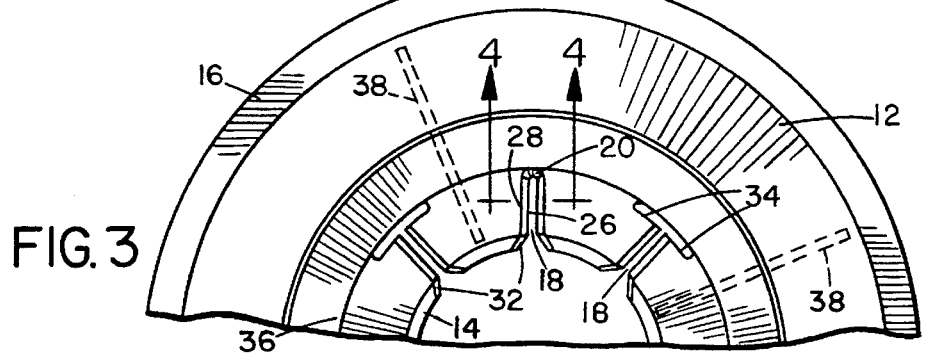
FIG. 3 is a partical top plan view of the cleaner.

As illustrated in FIGS. 1–3, a generally tubular or annular body 10 has a wall 12 with an upper rim 14 and a lower rim 16. Multiple slots 18 are distributed evenly around the circumference of body 10. A cauterizer blade may be drawn in a generally radial direction through a slot 18 to wipe it free of debris. Body 10 is made of any suitable rigid or semi-rigid material, such as plastic.

Each slot 18 extends from upper rim 14 toward lower rim 16, following any local curvature of wall 12, and terminates at a slot bottom 20. Slot bottom 20 may be rounded. Each slot 18 has two slot sidewalls 30 that extend through the thickness of wall 12 between the inner and outer surfaces 22 and 24, respectively, of wall 12. Each slot 18 has two inner edges 26 at inner surface 22. Inner edges 26 are equidistant from each other at all points along their lengths, but they are not precisely parallel because they follow the local curvature of wall 12. The distance between inner edges 26 defines a slot width. The slot width is approximately equal to the width of cauterizer blade 17 and is preferably less than about two millimeters. To conform to the shape of cauterizer blade 17, the slots are relatively long and narrow, with the slot length being at least eight times as great as the slot width.

Figure 4:
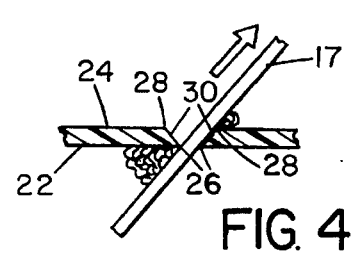
FIG. 4 is an enlarged sectional view taken along line 4—4 of FIG. 3, showing the scraping or wiping action.

Each slot 18 also has two outer edges 28 at outer surface 24 that, like inner edge 26, are equidistant from each other. The distance between outer edges 28 is greater than the slot width, thereby giving a beveled appearance to slot sidewalls 30. This arrangement provides a chisel-like or wiper-like action for enhancing removal of debris from cauterizer blade 17. It also promotes effective cleaning of cauterizer blade 17 over a wide range of pivotal angles, such as the extreme pivotal angle shown in FIG. 4 of approximately 45 degrees with respect to a radius of body 10. Each slot 18 also has a "V"-shaped notch 32 at upper rim 14 for guiding cauterizer blade 17 into the slot 18.

When cauterizer blade 17 is drawn through a slot 18, each of the two surfaces of cauterizer blade 17 contacts an inner edge 26. If the material from which wall 12 is made provides sufficient resiliency, the portions of wall 12 immediately adjacent slot 18 flex slightly to provide frictional sealing between cauterizer blade 17 and inner edges 26. Slot 18 may further include side portions 34 that extend perpendicularly to edges 26 and 28, thereby forming a "T"-shaped slot 18, to facilitate flexure of the portions of wall 12 adjacent slot 18.

Although body 10 may be generally described as tubular because it has open ends, body 10 is more specifically described as dome-shaped because the majority of outer surface 24 of wall 12 is convex. A portion of outer surface 24, however, preferably includes a concave area or trough 36 for catching any residual debris. (In the illustrated embodiment, the contours of inner surface 22 correspond inversely to those of outer surface 24 because the thickness of wall 12 is uniform.)

Four supports 38 inside body 10 provide additional strength and rigidity. The lower portion of each support 38 is coplanar with lower rim 16.

A double-sided adhesive sheet 40 is adhesively attached to lower rim 16 and the lower portions of supports 38. Sheet 40 has upper and lower adhesive-coated surfaces 42 and 44, respectively. A silicone-coated backing sheet 46 covers lower adhesive-coated surface 44 to protect it prior to use.

To use the present invention, backing sheet 46 is peeled away to expose lower adhesive-coated surface 44. Body 10 is adhered to a surgical drape 48 by pressing it against drape 48 at a convenient location. As the cautery device is used on the patient, cauterizer blade 17 may be cleaned by inserting it in a vertically downward direction into a conveniently located one of slots 18 and then withdrawing it in a radially outward direction. Inner edges 26 wipe away debris clinging to blade 17, as described above. The loose debris falls inside body 10 and is trapped on upper adhesive-coated surface 42.

Obviously, other embodiments and modifications of the present invention will occur readily to those of ordinary skill in the art in view of these teachings. Therefore, this invention is to be limited only by the following claims, which include all such other embodiments and modifications when viewed in conjunction with the above specification and accompanying drawings.

What is claimed is:

1. A cauterizer blade wiper, comprising:

a tubular body having a wall between first and a second rims, said wall having a wall inner surface, a wall outer surface, and a plurality of slots, each slot extending from said first rim toward said second rim and terminating at a slot bottom, the distance from said first rim to said slot bottom defining a slot length; and a double-sided adhesive sheet having first and second adhesive surfaces, said first adhesive surface adhesively attached to said second rim, said second surface having a pressure-sensitive adhesive thereon and a peelable backing sheet covering said pressure-sensitive adhesive for selectively exposing said pressure-sensitive adhesive.

2. The cauterizer blade wiper claimed in claim 1, wherein each slot has a notch at said first rim of said wall for guiding said cauterizer blade.

3. The cauterizer blade wiper claimed in claim 1, wherein each slot has two equidistant inner edges on said wall inner surface for wiping said cauterizer blade and two outer edges on said wall outer surface, said inner edges separated by a slot width, and said outer edges separated by a distance greater than said slot width.

4. The cauterizer blade wiper claimed in claim 1, wherein the slot has a slot width and the ratio of said slot length to said slot width is a least eight.

5. The cauterizer blade wiper claimed in claim 1, wherein a portion of said wall inner surface adjacent each slot is concave.

6. The cauterizer blade wiper claimed in claim 1, wherein a portion of said wall outer surface has an annular trough for catching debris therein.

7. The cauterizer blade wiper claimed in claim 1, wherein each slot has inner edges and outer edges and a portion at said slot bottom perpendicular to said inner and outer edges.

8. A cauterizer blade wiper, comprising:

a tubular body having a wall between first and a second rims, said wall having a wall inner surface, a wall outer surface, and a plurality of slots distributed evenly around the circumference of said body, each slot extending from said first rim toward said second rim and terminating at a slot bottom, the distance from said first rim to said slot bottom defining a slot length;

each said slot having a "V"-shaped notch at said first rim of said wall for guiding said cauterizer blade;

each said slot having two equidistant inner edges on said wall inner surface for wiping said cauterizer blade and two outer edges on said wall outer surface, said inner edges separated by a slot width, and said outer edges separated by a distance greater than said slot width.

* * * * *